US00PP11797P2

(12) United States Plant Patent
Westhoff

(10) Patent No.: US PP11,797 P2
(45) Date of Patent: Mar. 6, 2001

(54) PETUNIA PLANT NAMED 'WESARMEN'

(75) Inventor: Heinrich Westhoff, Südlohn-Oeding (DE)

(73) Assignee: Gartenbau-Spezialkulturen, Sudlohn-Ouding (DE)

( * ) Notice: Subject to any disclaimer, the term of this patent is extended or adjusted under 35 U.S.C. 154(b) by 0 days.

(21) Appl. No.: 09/324,084

(22) Filed: Jun. 1, 1999

(51) Int. Cl.[7] ..... A01H 5/00
(52) U.S. Cl. ..... Plt./356
(58) Field of Search ..... Plt./356

(56) References Cited

U.S. PATENT DOCUMENTS

P.P. 8,879 * 9/1994 Danziger ..... Plt./356

OTHER PUBLICATIONS

UPOV CD–ROM, Petunia named 'Wesaren', QZ, PBR 960911, 2000.*

* cited by examiner

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of Petunia plant named 'Wesarmen', characterized by its compact plant habit and short internodes; small, dark green, rounded leaves; numerous purple flowers with intense dark purple net-like venation; cascading and freely branching growth habit; relatively early flowering; and good weather tolerance, particularly tolerant to rain, wind and low temperatures.

1 Drawing Sheet

BACKGROUND OF THE INVENTION

The present invention relates to a new and distinct cultivar of Petunia plant, botanically known as *Petunia axillaris*, and hereinafter referred to by the cultivar name Wesarmen.

The new Petunia is a product of a planned breeding program conducted by the Inventor in Südlohn-Oeding, Germany. The new Petunia originated from a cross made by the Inventor in 1996 of the seedling selection of *Petunia axillaris* identified as Sylvana konigsblau as the female, or seed, parent with the seedling selection of *Petunia axillaris* identified as Sylvana 95/106 as the male, or pollen, parent.

Asexual reproduction of the new cultivar by terminal cuttings taken at Südlohn-Oeding, Germany, has shown that the unique features of this new Petunia are stable and reproduced true to type in successive generations.

SUMMARY OF THE INVENTION

Plants of the cultivar Wesarmen have not been observed under all possible environmental conditions. The phenotype may vary somewhat with variations in environments such as temperature, light intensity, daylength, and fertility level without, however, any variance in genotype.

The following traits have been repeatedly observed and are determined to be the unique characteristics of 'Wesarmen'. These characteristics in combination distinguish 'Wesarmen' as a new and distinct cultivar:

1. Compact plant habit and short internodes.

2. Small, dark green, rounded leaves.

3. Numerous purple flowers with intense dark purple net-like venation.

4. Cascading and freely branching growth habit.

5. Relatively early flowering.

6. Good weather tolerance, particularly tolerant to rain, wind and low temperatures.

Plants of the cultivar Wesarmen can be compared to plants of the nonpatented Surfinia Hot Pink. In side-by-side comparisons conducted in Südlohn-Oeding, Germany, plants of the cultivar Wesarmen differ from plants of the cultivar Surfinia Hot Pink in the following characteristics:

1. Plants of the new Petunia are more compact and have shorter internodes than of plants of the cultivar Surfinia Hot Pink.

2. Leaves of plants of the new Petunia are smaller and more rounded than leaves of plants of the cultivar Surfinia Hot Pink.

3. Plants of the new Petunia flower earlier than plants of the cultivar Surfinia Hot Pink.

4. Plants of the new Petunia have smaller sepals than plants of the cultivar Surfinia Hot Pink.

Plants of the cultivar Wesarmen can be compared to plants of the nonpatented Surfinia Purple. In side-by-side comparisons conducted in Südlohn-Oeding, Germany, plants of the cultivar Wesarmen differ from plants of the cultivar Surfinia Purple in the following characteristics:

1. Plants of the new Petunia are not as broad and as spreading as of plants of the cultivar Surfinia Purple.

2. Leaves of plants of the new Petunia are darker green, shorter, more rounded and have longer petioles than leaves of plants of the cultivar Surfinia Purple.

3. Plants of the new Petunia have smaller but more flowers than plants of the cultivar Surfinia Purple.

4. Plants of the new Petunia and Surfinia Purple differ in flower color.

5. Plants of the new Petunia have larger and darker green sepals than plants of the cultivar Surfinia Purple.

6. Plants of the new Petunia have longer peduncles than plants of the cultivar Surfinia Purple.

7. Plants of the new Petunia exhibit better weather tolerance than plants of the cultivar Surfinia Purple.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of typical plants of the new Petunia grown in a hanging basket. Flower and foliage colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown under greenhouse conditions which closely approximate commercial production conditions in Südlohn-Oeding, Germany, with average day and night temperatures of 23° C. and 16° C., respectively with an average light level ranging from 3,000 to 5,000 lux. Observations were made eight to ten weeks after planting cuttings.

Botanical classification: *Petunia axillaris* cultivar Wesarmen.

Parentage:

*Female parent.*—*Petunia axillaris* seedling selection identified as Sylvana konigsblau, not patented.

*Male parent.*—*Petunia axillaris* seedling selection identified as Sylvana 95/106, not patented.

Propagation:

*Type cutting.*—Terminal vegetative cuttings.

*Time to initiate and develop roots.*—About 14 days at 20° C. soil temperature.

*Rooting habit.*—Numerous, fine, fibrous, and well-branched.

Plant description:

*Form.*—Compact; indeterminate, cascading, viscid, glandular pubescent. Appropriate for hanging baskets and balcony containers.

*Branching habit.*—Freely basally branching; with pinching lateral branches typically form at every node.

*Plant height* (*from soil level to top of plant plane*).—About 20 cm.

*Area of spread.*—About 55 to 60 cm.

*Vigor.*—Moderate.

*Lateral branches.*—Diameter: About 3 to 4 mm. Internode length: About 2.4 cm. Texture: Densely pubescent. Color: 144A: apex of shoot with anthocyanin.

*Foliage description.*—Leaves simple, generally symmetrical and long persisting. Leaf arrangement alternate. Leaves somewhat fleshy, glandular. Foliage tolerate to wind and rain damage. Length: About 3.7 cm. Width: About 3.4 cm. Aspect: Typically horizontal. Shape: Rounded. Apex: Slightly acute. Base: Attenuate. Margin: Entire. Texture: Slightly pubescent on both surfaces. Color: Young foliage, upper surface: 137A. Young foliage, lower surface: 137C. Mature foliage, upper surface: 137A. Mature foliage, lower surface: 137C. Venation, both surfaces: 144A. Petiole: Length: About 8 mm. Diameter: About 2.7 mm. Color: 144A.

Flower description:

*Flower type and habit.*—Single axillary salverform flowers that face upwards. Calyx five-parted, petals united into a flower tube. Faint fragrance typical of Petunia. Persistent. Early flowering.

*Natural flowering season.*—Long day responsive, continuously flowers from spring through fall; hardy to −3° C.

*Quantity.*—Very freely flowering with numerous flowers per plant.

*Flower buds.*—Length: About 4.4 cm. Diameter: About 8.4 mm. Shape: Linear to oblong. Color: Apex: 144B. Mid-section and base: 79A to 79B.

*Corolla.*—Diameter: About 5.9 cm. Flower tube length: About 3 cm. Flower tube diameter at distal end: About 1.15 cm. Flower tube diameter at proximal end: About 4 mm. Petal length from throat: About 2.6 cm. Petal width: About 3.4 cm. Petal quantity: Five, fused. Petal shape: Obverse. Petal apex: Rounded and slightly dentate. Petal margin: Entire or slightly denatate or undulate. Texture: Smooth and satiny. Color: Purple with intense dark purple net-like venation. Petal, upper surface, when opening: Venation, 79A to 79B; background and margin, 78A to 78B. Petal, lower surface, when opening: Venation, 79C; background and margin, 78C. Petal, upper surface, opened flower: Venation, 79A to 79B; background and margin, 78A. With further development, venation, 83A; background and margin, 86C to 86D. Petal, lower surface, opened flower: Venation, 79C to 79D; background and margin, 78D Flower throat (inside): 79A. Flower throat, vein: 79A. Flower tube (outside): 79B. Flower tube, vein: 200A to 200B.

*Sepals.*—Quantity: Five. Length: About 2.25 cm. Width: About 1 cm. Shape: Elliptic. Apex: Obtuse. Margin: Entire. Aspect: Upright. Color: Upper surface: 137A, dulled. Lower surface: 137C, dulled.

*Peduncle.*—Strength: Wiry, flexible. Angle: Mostly upright. Length: Long, about 5 cm. Diameter: About 2 mm. Color: 144A.

*Reproductive organs.*—Stamens: Stamen number: Five. Anther shape: Four-parted, kidney-shaped. Anther size: About 2.7 mm. Anther color: 83C to 83D. Pollen amount: Moderate. Pollen color: 91A. Pistils: Pistil length: About 2.5 cm. Stigma shape: Inverted triangle. Stigma color: 147B. Style length: About 2 cm. Style color: 145C. Ovary color: 145A.

Weather tolerance: Good tolerance to rain and wind has been observed. The new Petunia can withstand low temperatures to about −3° C.

Disease resistance: Resistance to diseases common to Petunia has not been observed.

Seed production: Seed production has not been observed.

It is claimed:

1. A new and distinct cultivar of Petunia plant named 'Wesarmen', as illustrated and described.

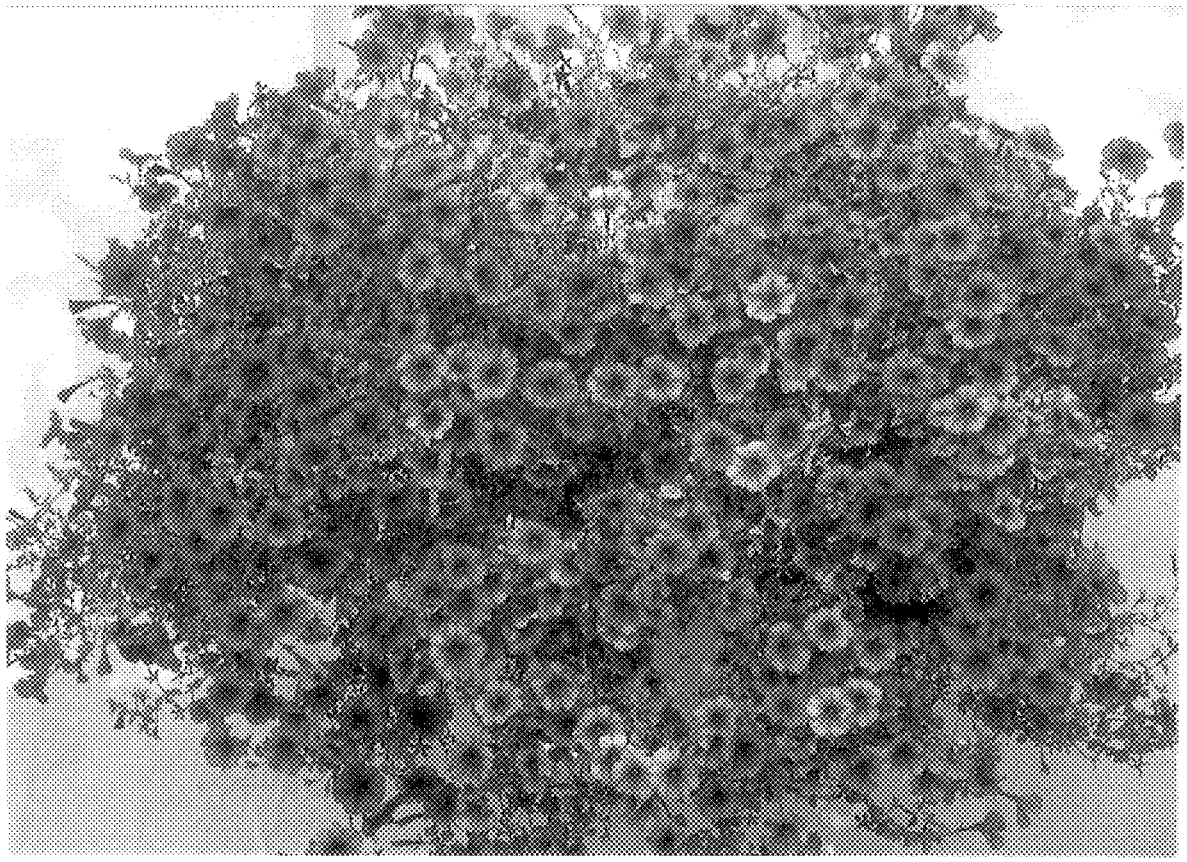

* * * * *